US010111725B2

(12) United States Patent
van den Dries et al.

(10) Patent No.: US 10,111,725 B2
(45) Date of Patent: Oct. 30, 2018

(54) MASSAGE TOOL CASE

(71) Applicant: Rocktape, Inc., Campbell, CA (US)

(72) Inventors: Gregory van den Dries, Los Gatos, CA (US); Steven Capobianco, Highlands Ranch, CO (US)

( * ) Notice: Subject to any disclaimer, the term of this patent is extended or adjusted under 35 U.S.C. 154(b) by 0 days.

(21) Appl. No.: 15/271,027

(22) Filed: Sep. 20, 2016

(65) Prior Publication Data

US 2018/0079572 A1    Mar. 22, 2018

(51) Int. Cl.
*A61B 50/31*    (2016.01)
*A61H 15/00*    (2006.01)
*A61H 37/00*    (2006.01)
*B65D 25/10*    (2006.01)
(Continued)

(52) U.S. Cl.
CPC .............. *A61B 50/31* (2016.02); *A61B 50/30* (2016.02); *A61H 15/0092* (2013.01); *A61H 37/00* (2013.01); *B65D 25/108* (2013.01); *A61B 2050/005* (2016.02); *A61B 2050/3008* (2016.02); *A61B 2050/311* (2016.02)

(58) Field of Classification Search
CPC ... A61B 50/31; A61B 2050/311; A61H 15/00; A61H 15/0092; A61H 37/00; B65D 71/70; B65D 85/20; B65D 85/24; B65D 85/28; B65D 25/10; B65D 25/108
USPC ................ 206/349, 363–370, 372, 373, 438, 206/570–572, 733, 734, 763, 486–490; 211/60.1–70.8
See application file for complete search history.

(56) References Cited

U.S. PATENT DOCUMENTS 1,456,613 A  *  5/1923  Bartels ...................... A47F 7/03
                                                  206/734
4,111,302 A  *  9/1978  Roth ......................... A61F 6/14
                                                  206/363
(Continued)

FOREIGN PATENT DOCUMENTS

WO        2015126405 A1    8/2015

OTHER PUBLICATIONS

Capobianco, et al, Multi-layered Massage Tool, Unpublished International Patent Application # PCT/US2016/0019239, International Filing Date of Feb. 24, 2016.
(Continued)

*Primary Examiner* — Bryon Gehman
(74) *Attorney, Agent, or Firm* — Young's Patent Services, LLC; Bruce A. Young

(57) ABSTRACT

An instrument assisted soft tissue mobilization (IASTM) system includes a substantially flat massage tool, such as an instrument-assisted soft tissue mobilization (IASTM) tool, and a case to hold the substantially flat massage tool in either a storage position or a display position. The case includes a structure with a top surface and the top surface has a recess shaped to receive and situate the first substantially flat tool in a horizontal position relative to the top surface. The structure also includes a slot shaped to receive and situate the substantially flat tool in an angled position extending away from the top surface. If the substantially flat massage tool is placed horizontally into the recess, the IASTM system is in the storage position. If the substantially flat massage tool is placed vertically into the slot, the IASTM system is in the display position.

20 Claims, 13 Drawing Sheets

(51) Int. Cl.
*A61B 50/30* (2016.01)
*A61B 50/00* (2016.01)

(56) References Cited

U.S. PATENT DOCUMENTS

| | | | | |
|---|---|---|---|---|
| 4,420,085 | A | * | 12/1983 | Wilson ................. A61M 5/002 |
| | | | | 206/370 |
| 4,590,926 | A | | 5/1986 | Courtin |
| 4,765,584 | A | * | 8/1988 | Lazaris .................... B25H 3/04 |
| | | | | 211/70.1 |
| 5,011,020 | A | * | 4/1991 | Stevens ................. A45C 13/02 |
| | | | | 206/438 |
| 5,275,281 | A | | 1/1994 | Ebeling |
| 5,351,819 | A | * | 10/1994 | Varon ............... B65D 5/48024 |
| | | | | 206/570 |
| 5,394,983 | A | * | 3/1995 | Latulippe ................. A61L 2/26 |
| | | | | 206/370 |
| 5,447,230 | A | * | 9/1995 | Gerondale .......... B65D 5/5002 |
| | | | | 206/363 |
| 5,544,753 | A | * | 8/1996 | Monica .............. A63B 23/0211 |
| | | | | 206/570 |
| 6,241,696 | B1 | | 6/2001 | York |
| D542,926 | S | | 5/2007 | Louis |
| 7,431,706 | B2 | | 10/2008 | Louis |
| D615,210 | S | | 5/2010 | Woodhams et al. |
| D632,400 | S | | 2/2011 | Bludorn |
| 7,975,857 | B2 | * | 7/2011 | Restis .................... A47L 19/02 |
| | | | | 211/70.7 |
| D665,916 | S | | 8/2012 | Zhang et al. |
| D677,394 | S | | 3/2013 | Grust et al. |
| D683,862 | S | | 6/2013 | Hartman |
| D731,072 | S | | 6/2015 | Dries et al. |
| RE45,657 | E | | 8/2015 | Cho |
| D752,238 | S | | 3/2016 | Stock |
| D753,317 | S | | 4/2016 | Eddy et al. |
| D757,281 | S | | 5/2016 | Hsieh |
| D792,600 | S | | 7/2017 | van den Dries et al. |
| D792,601 | S | | 7/2017 | van den Dries et al. |
| 2011/0172573 | A1 | | 7/2011 | Wallace |
| 2012/0100516 | A1 | | 4/2012 | Iwami et al. |
| 2014/0213944 | A1 | | 7/2014 | Kojima |
| 2014/0358045 | A1 | | 12/2014 | Tote |
| 2015/0231014 | A1 | | 8/2015 | Capobianco et al. |

OTHER PUBLICATIONS

Hedderman, R, An Interview with Dr. Kevin Laudner & A Tour of Illinois State University: Go Red Birds, Jul. 15, 2015, at least pp. 17-18, http://www.hurricanefitnessireland.com/blog/2015/7/7/an-interview-with-dr-kevin-laudner-at-illinois-state-university-go-red-birds, (retrieved on Sep. 20, 2016).

Van Den Dries, et al, Massage Tool, Unpublished Design U.S. Appl. No. 29/955,048, filed Jan. 20, 2016.

Van Den Dries, et al, Massage Tool, Unpublished Design U.S. Appl. No. 29/955,049, filed Jan. 20, 2016.

Chirobalance Spine & Sport, First look at RockBlades from RockTape (YouTube Video), May 3, 2016, https://www.youtube.com/watch?v=YK7la9USuZ0, Screenshot taken at 0:50 in the video on Sep. 23, 2017.

Rocktape, Rockblades web page, Mar. 6, 2016 (from Wayback Machine), retrieved from https://web.archive.org/web/20160506080648/http://www.rocktape.com:80/products/blades/? on Sep. 23, 2017.

* cited by examiner

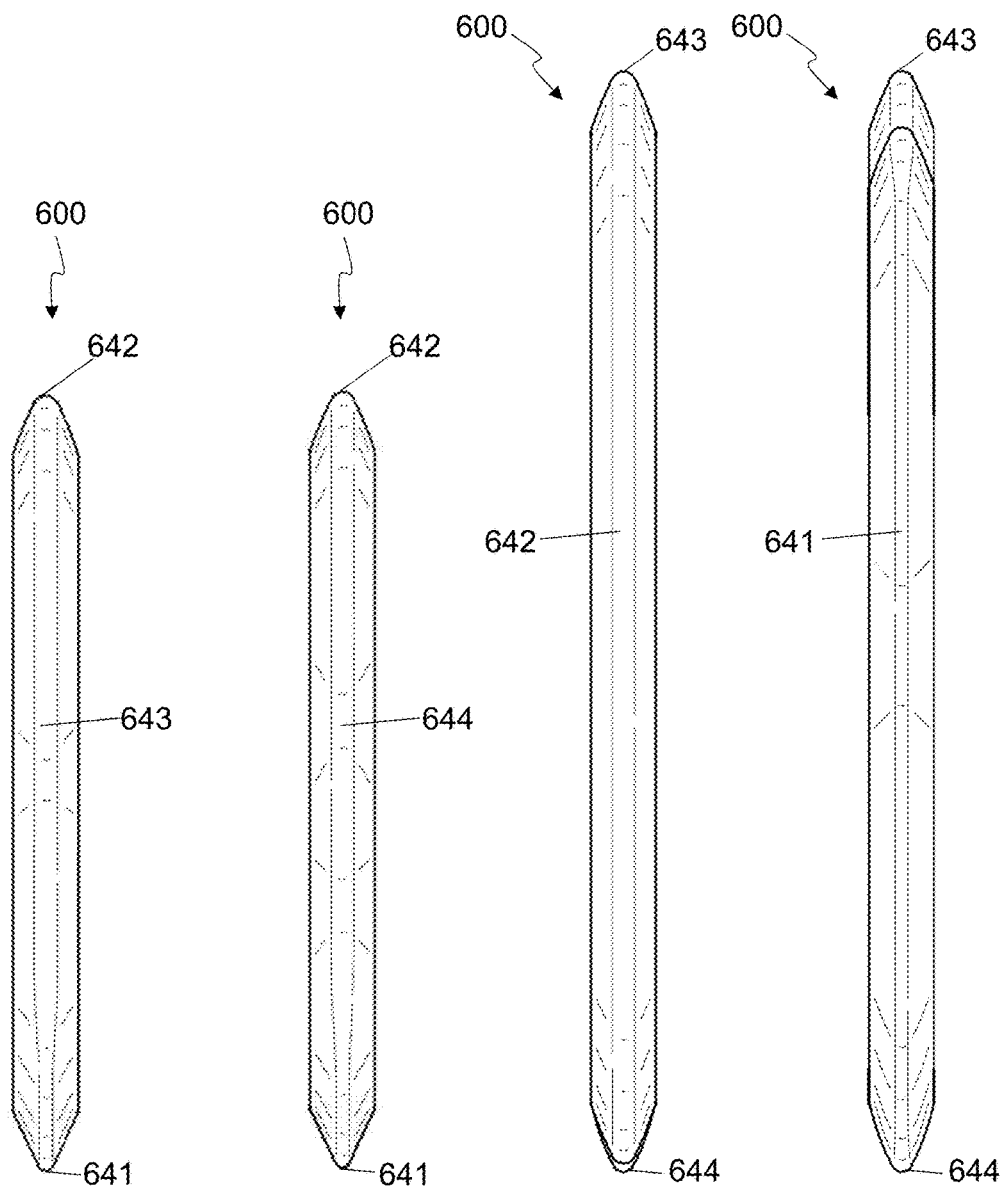

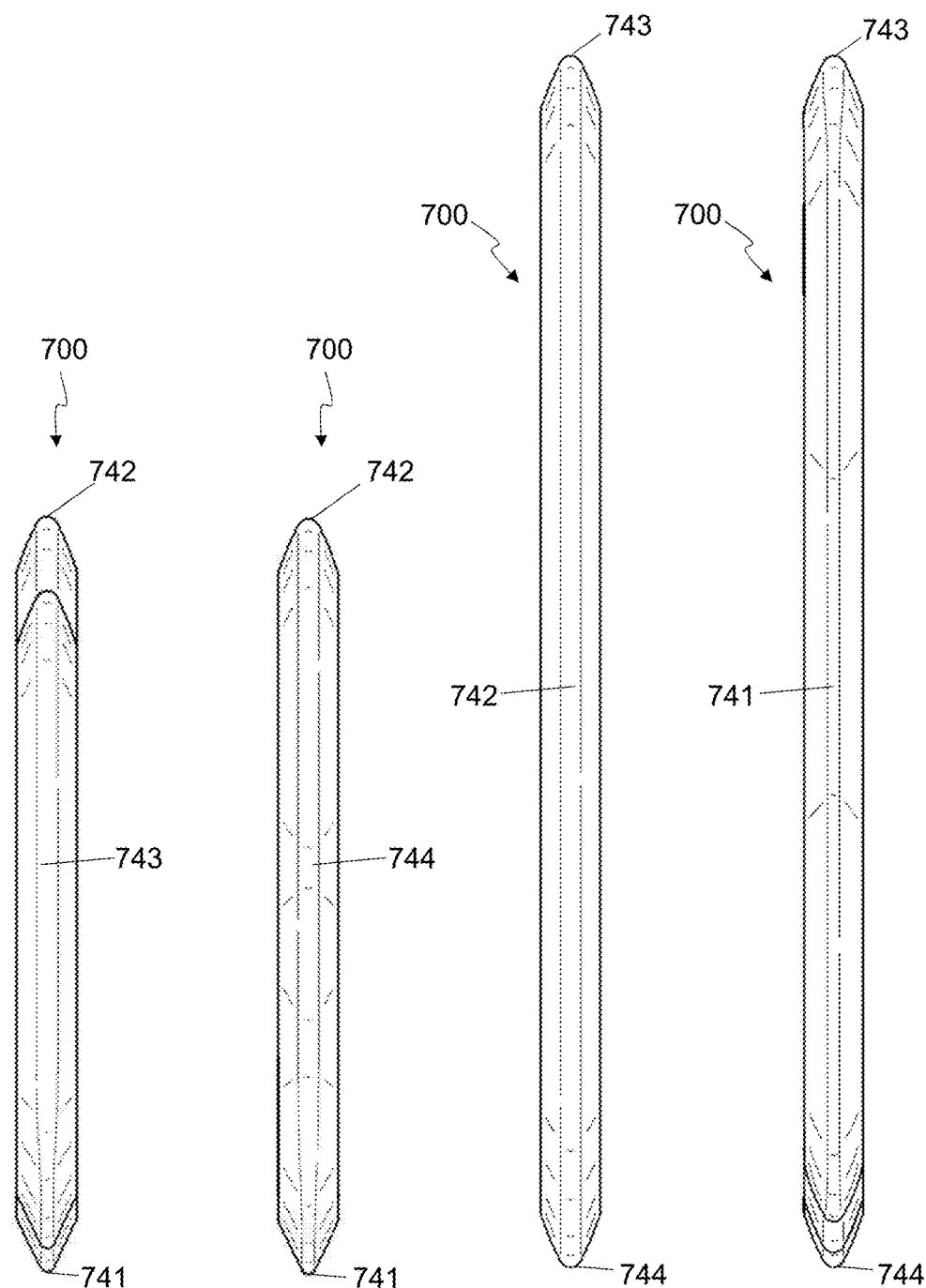

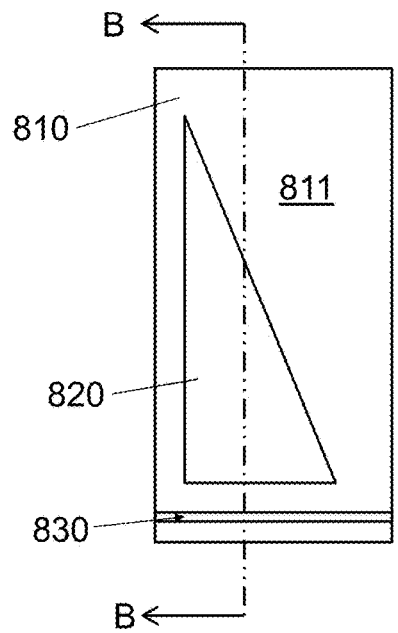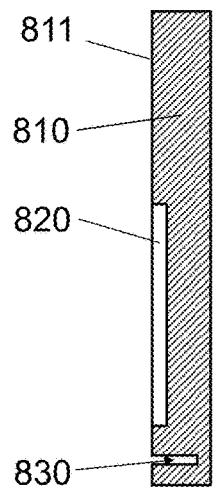
FIG. 8A   FIG. 8B
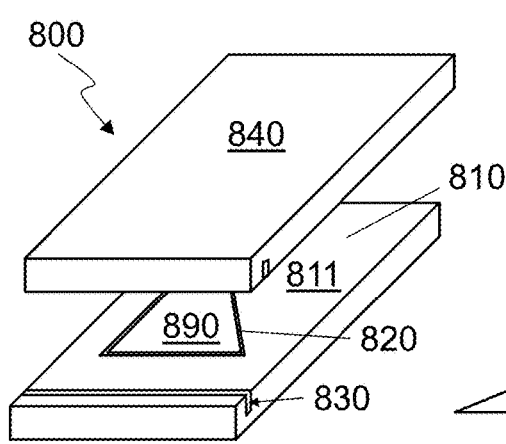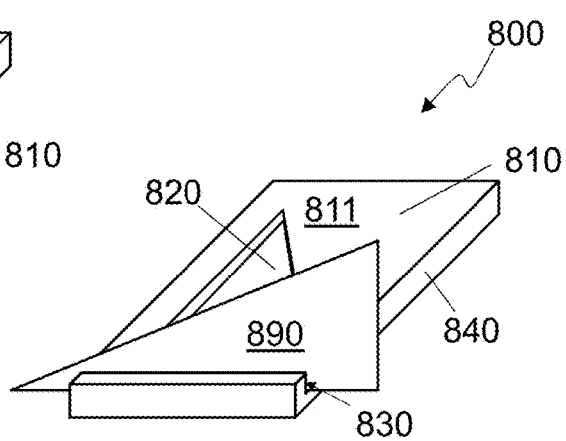
FIG. 8C   FIG. 8D

MASSAGE TOOL CASE

CROSS-REFERENCE TO RELATED APPLICATIONS

This application is related to International Patent Application PCT/US2016/0019239 filed on Feb. 24, 2016 and entitled MULTI-LAYERED MASSAGE TOOL, as well as U.S. Design patent application Ser. Nos. 29/552,048 and 29/552,049, both filed on Jan. 20, 2016 and entitled Massage Tool. All three of the aforementioned patent applications are incorporated by reference herein for any and all purposes.

BACKGROUND

Technical Field

The present subject matter relates to a case for tools, and more specifically, to a case for massage tools.

Background Art

Massage has long been used as a relaxation technique as well as a form of therapy for fatigue and many different musculoskeletal disorders. Massage involves manipulation of a person's body, and often targets one or more specific muscles and/or joints on the body, depending on the objective of the massage. Targeted tissues for various types of massage include muscles, tendons, ligaments, fascia, skin, lymphatic vessels, and organs of the gastrointestinal system. Many different techniques are used for massage, including static pressure, moving pressure, and vibration.

Different massage techniques are applied using various apparatus. In many types of massage, the massage therapist uses a part of their body to apply the massage, such as hands, fingers, elbows, knees, forearms, or feet. In some types of massage, the individual receiving the massage is positioned on an apparatus that positions the individual for the masseuse, or can even apply the massage directly to the individual. The apparatus can vary widely and range from a small object, such as a ball or block, that the individual lies, sits or stands on, to large complex massage machines, such as a massage chair, that hold the individual and mechanically perform the massage on the individual.

In some forms of massage such as myofascial release, fascial tissue manipulation, Gua sha, and the Graston Technique®, just to name a few, hand-held massage tools are commonly used. In many types of massage, the massage tools are used to stretch the fascia and release bonds between fascia, integument, and muscles, with a goal of eliminating pain and/or increasing a range of motion. The tools can be used to apply shear compression or tension in various directions, to roll over the skin, or for many other effects, depending on the type of massage and the specific objectives. Many times these tools are relatively flat, with an outer rim that is configured for various therapies of specific body parts. In some cases, these tools may be referred to as instrument-assisted soft tissue mobilization (IASTM) tools and the massage therapy may be referred to as IASTM therapy.

Such massage tools are often shipped and/or stored in cases that conform to the shape of the tool to keep the massage tools from shifting to prevent noise and potential damage to the massage tools. These cases often conform very closely to the shape of the tool and in some cases may make it difficult to easily grab the tool, especially if the massage therapist's hands are slick from various lotions and oils that may be used in conjunction with the massage therapy.

BRIEF DESCRIPTION OF THE DRAWINGS

The accompanying drawings, which are incorporated in and constitute part of the specification, illustrate various embodiments. Together with the general description, the drawings serve to explain various principles. In the drawings:

FIG. 6A-F show various views of a first embodiment of a massage tool;

FIG. 7A-F show various views of a second embodiment of a massage tool;

FIGS. 8A and 8B show top and cross-sectional views, respectively, of a second embodiment of a structure to hold tools in either a storage or display position;

FIG. 8C shows a perspective view of a second embodiment of a tool case with a tool in a storage position;

FIG. 8D shows a perspective view of the second embodiment of the tool case with the tool in a display position;

DETAILED DESCRIPTION

Figure 1A:
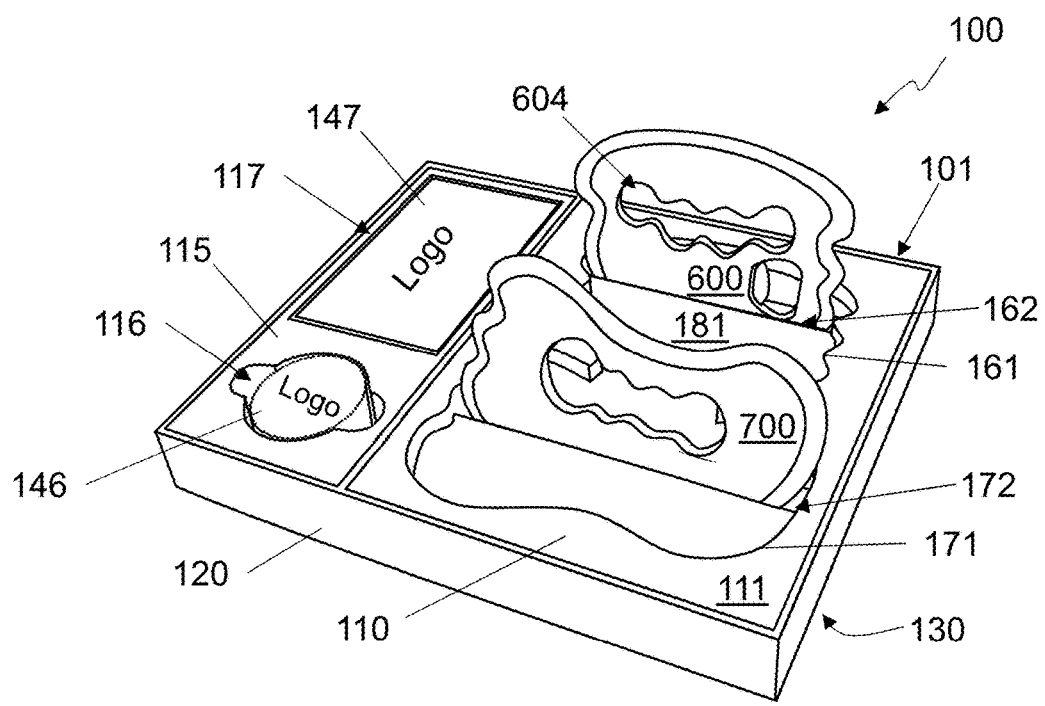
FIGS. 1A and 1B show perspective and side views, respectively, of an embodiment of an IASTM system with the IASTM tools in a display position.

In the following detailed description, numerous specific details are set forth by way of examples in order to provide a thorough understanding of the relevant teachings. However, it should be apparent to those skilled in the art that the present teachings may be practiced without such details. In other instances, well known methods, procedures, and components have been described at a relatively high-level, without detail, in order to avoid unnecessarily obscuring aspects of the present concepts. A number of descriptive terms and phrases are used in describing the various embodiments of this disclosure. These descriptive terms and phrases are used to convey a generally agreed upon meaning to those skilled in the art unless a different definition is given in this specification. Some descriptive terms and phrases are presented in the following paragraphs for clarity.

Substantially flat, as the term is used herein and in the claims, means that the thickness of the substantially flat apparatus is less than 20% of either of the other two dimensions, the width and the height. In some cases, the substantially flat apparatus may have sides that parallel to each other, although parallel sides are not required to be substantially flat. The apparatus may have various holes, textured portions, varying thicknesses, and/or dimples, and still be considered substantially flat.

A horizontal position, as it refers to a substantially flat apparatus, means that a plane perpendicular to a thickness of the apparatus (e.g. parallel with the width and height) is parallel, or at least within a 30 degree angle of parallel, to a reference surface. A vertical position, as it refers to a substantially flat apparatus, means that the plane perpendicular to a thickness of the apparatus is perpendicular, or at least within a 45 degree angle of perpendicular, to a reference surface.

Magnetic material is a material that may be attracted to a magnet. Magnetic material may or may not remain magnetized without an external magnetic field. Examples of magnetic material include a magnet, steel, or other ferromagnetic materials.

A magnet is a magnetic material that generates a magnetic field, or is magnetized, even if the magnet is not being subjected to an external magnetic field. A magnet may also be referred to as a permanent magnet.

As mentioned in the background section, use of instrument-assisted soft tissue mobilization (IASTM) tools can be an effective therapy for a variety of pathologies. In many cases, IASTM tools are substantially flat tools and can be made from a variety of materials including, but not limited to, buffalo horn, various types of stone, plastics such as polycarbonates, or metals such as stainless steel. IASTM tools usually have smooth surfaces to allow them to slide over the skin of a person with a minimum amount of friction and without causing any abrasions.

Many therapists use a variety of IASTM tools for various purposes and for various areas of the body that have different sizes and shapes. Keeping the tools organized can be very important so that the therapist can easily access the desired tool without any searching or fumbling through other tools. In addition, oils, lotions, salves, or other types of lubricants are often used in IASTM therapies which can make the IASTM tools slippery and hard to grab, especially given the smooth surfaces of many IASTM tools.

IASTM tools can be organized like any other set of tools, including putting them in a tool box. But the practice of IASTM therapy demands that the tools be readily accessible and easily picked up without wasting a lot of time fumbling with the IASTM tool. In addition, IASTM tools often need to be stored and/or transported between locations. A container optimized for storing and/or transporting the IASTM tools will keep the IASTM tools from moving around and banging into each other as the container is transported. It will also tend to minimize the volume required to store the tools for convenience in storage/transporting and reduced cost in shipping. Such containers usually tightly fit around the IASTM tools to minimize movement, which makes it difficult to remove them from the container.

Thus, containers optimized for storing and/or transporting IASTM tools are not very useable for organizing IASTM tools during a therapy session. The tightly fitting recesses in the packing material make it difficult to grab the IASTM tools, especially if the IASTM tools are coated by a lubricant, such as oil or lotion. A case designed to display the IASTM tools in such a way to make each tool easy to identify and grab will be optimized to allow for actual use of the IASTM tools in a therapy session. In some embodiments, the display case exposes much of the surface of each IASTM tool and makes gripping features of the tool readily accessible. The fact that much of the IASTM tools are exposed helps to make it easy to identify each IASTM tool and makes it easy to remove the IASTM tools from the display case.

Embodiments of a tool case that can function both as a storage/transporting container and as a display case for IASTM tools are described herein. In one embodiment, the tool case is box-shaped with a structure that is configured to hold the IASTM tools in at least two different positions. The structure has at least one recess that can hold one or more substantially flat IASTM tools in a horizontal position for storage/transporting, and slots for holding the IASTM tools in a vertical position for display/use. A recess is shaped to fit an individual IASTM tool and hold it in position and is about the same depth as the thickness of the IASTM tool. The embodiment of the tool case also includes a lid that can be closed over the IASTM tools to keep them from coming loose as the tool case is jostled. The lid has a second position that exposes the structure and allows an IASTM tools to be removed from its recess.

The structure of the embodiment also has a slot for each IASTM tool that can hold the tool in a vertical position extending out of the box. This allows the IASTM tools to be easily identified and accessed. The slots in the embodiment are located within the recess(es) in the structure to minimize the footprint of the structure. At least some of the gripping structures of the IASTM tools, such as finger holes or dimples, are exposed when the IASTM tools are in the slots to facilitate easy grasping and removal of the tools from the tool case.

Embodiments of the tool case may include additional recesses to hold accessories such as wipes, lubricants, or other accessories useful in the IASTM therapy. The structure holding the IASTM tools and accessories in the embodiment of the tool case is injection molded polycarbonate with at least one recess that is shaped to accept one or more substantially flat IASTM tools in a horizontal position such that the tools do not extend outside of the box shape of the tool case and they can be covered by the lid.

An embodiment of an IASTM system includes the tool case described above as well as one or more IASTM tools. The IASTM system can also include one or more accessories, such as wipes and lotion. The IASTM system can be used in an embodiment of a method where the tool case is opened and the IASTM tools are removed from their recesses and inserted into their respective slots for display/use. The appropriate IASTM tool to use for applying an IASTM therapy to a particular portion of a human body can then be removed from the tool case and utilized in the therapy. The accessory, such as lotion, can be removed from its recess in the tool case and used in conjunction with the IASTM tool for the IASTM therapy.

Reference now is made in detail to the examples illustrated in the accompanying drawings and discussed below.

Figure 1B:
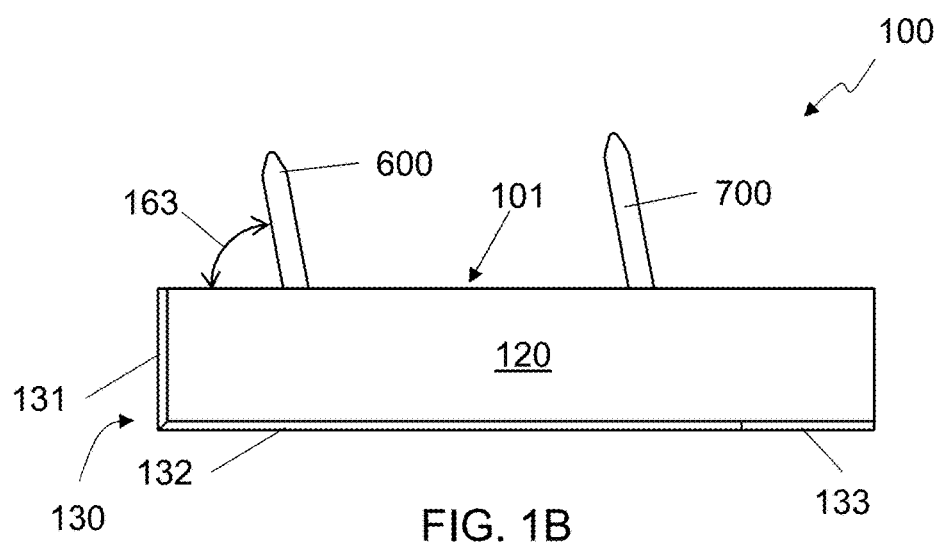
Figure 1C:
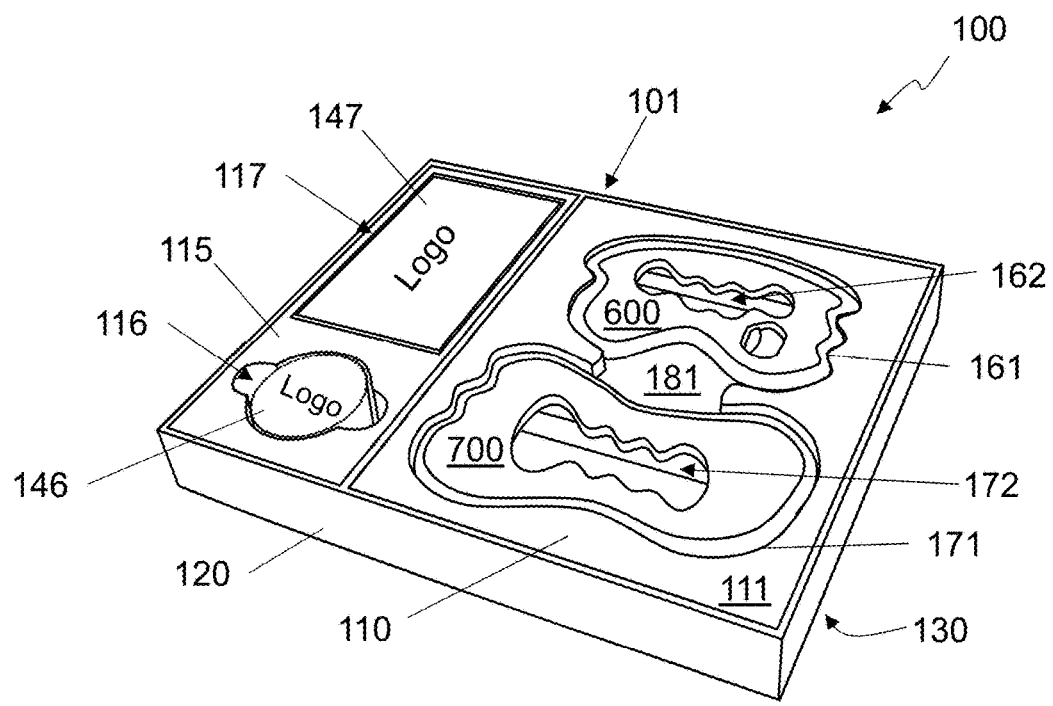
FIGS. 1C and 1D show perspective and side views, respectively, of the embodiment of the IASTM system with the IASTM tools in a storage position.
Figure 1D:
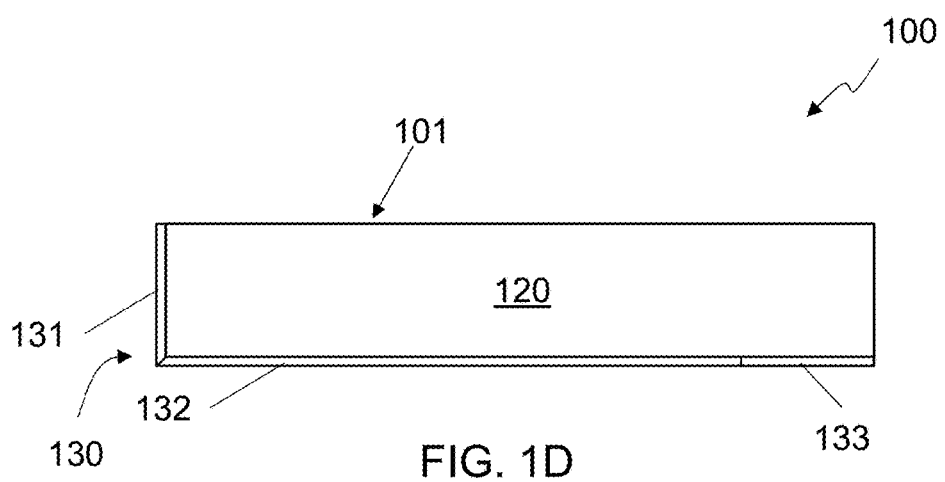

FIGS. 1A and 1B show perspective and side views, respectively, of an embodiment of an IASTM system 100 with the IASTM tools 600, 700 in a display position. The display position also positions the IASTM tools 600, 700 for easy access by the therapist during a session. FIGS. 1C and 1D show perspective and side views, respectively, of the embodiment of the IASTM system 100 with the IASTM tools 600, 700 in a storage position. The storage position may also be used for shipment of the IASTM system 100.

The following discussion applies to the IASTM system 100 and unless otherwise specified, can apply to any of FIG. 1A-1D.

The IASTM system 100 includes a first substantially flat massage tool, such as the first IASTM tool 600, and a case 101. In some embodiments, the IASTM system 100 includes additional substantially flat massage tools, such as the second IASTM tool 700. The case 101 includes a structure 110 with a top surface 111. The top surface 111 has a recess 181 shaped to receive and situate the first substantially flat tool 600 in a horizontal position relative to the top surface 111. The embodiment shown in FIG. 1A-D has a single recess 181 that includes two portions, a first portion 161 shaped to receive and situate a first IASTM tool 600, and a second portion 171, shaped to receive and situate a second IASTM tool 700. Thus the recess 181 is shaped to also receive and situate a second substantially flat tool 700 in a horizontal position relative to the top surface 111. In other embodiments, a separate recess may be used for each tool, and in yet other embodiments, a single recess may be configured to receive and situate more than two tools. Receive and situate means that the tool is held in a particular position and is unable to make contact with other tools in the case 101. In some embodiments, the recess 181 may hold the substantially flat tool in such a way that the tool is unable to move more than 5 millimeters (mm) in any direction parallel to the top surface 111. The recess 181 can have any depth, constant or varying, in various embodiments, but in at least some embodiments, the recess 181 has a depth between 120% and 95% of a thickness of the substantially flat tool 600, 700.

The structure 110 also includes a first slot 162 shaped to receive and situate the substantially flat tool 600 in an angled position extending away from the top surface 111, and a second slot 172 shaped to receive and situate the second substantially flat tool 700 in a second angled position extending away from the top surface 111. The tools 600, 700, when in their respective slots 162, 172, may be referred to as having a vertical position with respect to the top surface 111 of the structure 110. In embodiments, the slots 162, 172 are configured to hold their respective substantially flat tool 600, 700 at an angle 163 from the top surface 111 of between 45 and 135 degrees. The slots 162, 172 can be located anywhere in the structure 110, depending on the embodiment, but in the embodiment shown in FIG. 1A-1D, both the first slot 162 and the second slot 172 are disposed completely within the recess 181. The slots can have any depth, depending on the embodiment, but in at least some embodiments, the slot 162 has a slot depth configured to expose a gripping structure, such as finger hole 604 of the substantially flat massage tool 600, when the substantially flat massage tool 600 is inserted into the slot 162. In some embodiments, the slot 162 has a slot depth of between 15% and 35% of a height the substantially flat tool 600 and a slot width that does not exceed 200% of the thickness of the substantially flat tool 600.

The case 101 of the embodiment shown also includes a box 120 separated into a first cavity and a second cavity. The first cavity is configured to accept the structure 110, and the case 101 has the structure 110 inserted therein. The case 101 also includes an additional structure 115 configured to fit in the second cavity and inserted therein. The additional structure 115 also has a top surface with a third recess 116 shaped to receive and situate an accessory 146. The IASTM system 100 includes the accessory 146 which is inserted into the third recess 116. In some embodiments, the additional structure 115 also has a fourth recess 117 shaped to receive and situate an additional accessory 147. In some embodiments of the IASTM system 100, the additional accessory 147 is inserted into the fourth recess 117. The IASTM system 100 may include any type of accessory, but in some embodiments the accessories 146, 147 are selected from a group consisting of wipes, tissues, massage oil, lotion, skin moisturizer, hand sanitizer, kinesiology tape, bandages, and antibiotic cream. The accessories 146, 147 may be branded with a logo of the company marketing the IASTM system 100 in some embodiments.

The case 101 also includes a cover 130 in some embodiments. In the embodiment shown, the cover 130 is hingedly attached to the box 120 and includes three sections, a first section 131, a second section 132, and a third section 133, that are hingedly attached to each other. The cover 130 is shown in an open position that exposes the tools 600, 700 and folds the sections 131, 132, 133 against the back and bottom of the box 120. The cover 130 may be in either an open position (as shown in FIG. 1C-D) or a closed position (as shown in FIG. 2A-B) when the IASTM tools 600, 700 are in the storage position.

As shown in FIG. 1B, when the IASTM tools 600, 700 are inserted into their respective slots 162, 172 of the embodiment of the case 101, the IASTM tools 600, 700 extend away from the top surface 111 of the structure 110 and extend above a top of the box 120. As further shown in FIG. 1D, when the IASTM tools 600, 700 are placed in the recess 181 of the embodiment of the case 101, the IASTM tools 600, 700 do not extend above the top of the box 120.

Figure 2A:
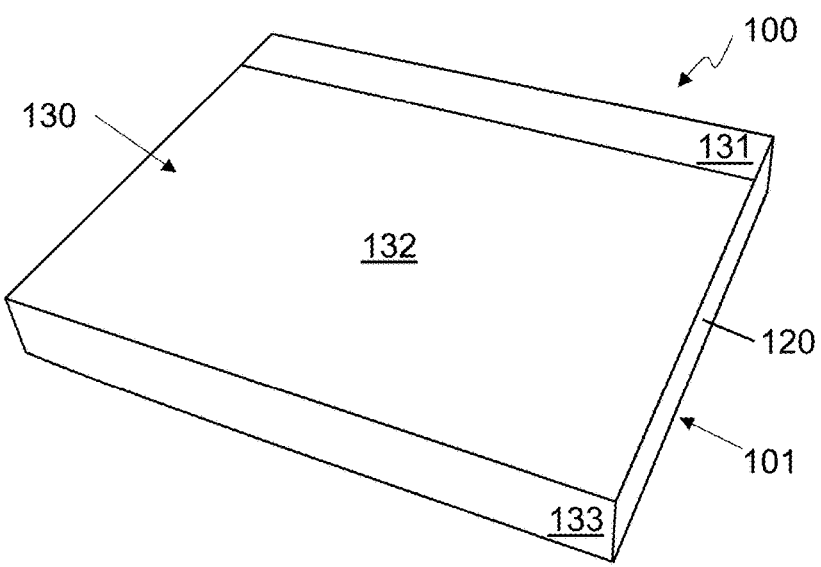
FIGS. 2A and 2B show perspective and side views, respectively, of the embodiment of the IASTM system with a cover if the tool case in a closed position.
Figure 2B:
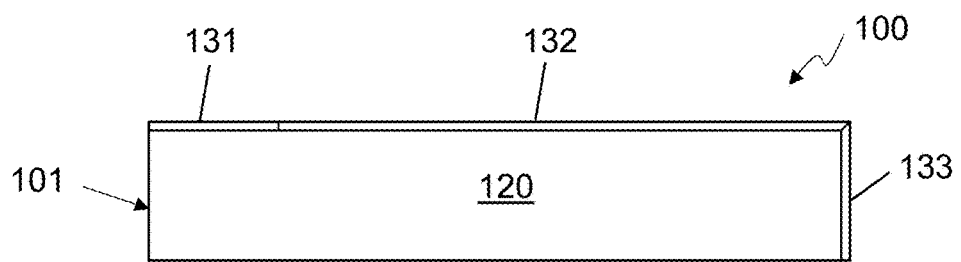

FIGS. 2A and 2B show perspective and side views, respectively, of the embodiment of the IASTM system 100 with the cover 130 of tool case 101 in a closed position. The cover 130 may also be referred to as a lid 130. The cover 130 is configured to alternately mate with the box 120 in a first position that covers the recess 181 and the slots 162, 172, and a second position to expose the slots 162, 172. The embodiment of the lid 130 is divided into a first section 131, a second section 132, and a third section 133. A rear top edge of the box 120 is hingedly attached to an inner edge of the first section 131 of the lid 130, an outer edge of the first section 131 of the lid 130 is hingedly attached to an inner edge of the second section 132 of the lid 130, and an outer edge of the second section 132 of the lid 130 is hingedly attached to an inner edge of the third section 133 of the lid 130. In the embodiment shown, the first section 131 of the lid and the third section 133 of the lid 130 each have a length about equal to a height of the box 120, and the second section 132 of the lid 130 has a length about equal to a difference between the length of the box 130 and the height of the box 120.

The lid 130 is configured to have an open position, as shown in FIG. 1A-D, with the first section 131 of the lid 130 folded against a back wall of the box 120, and the second section 132 and the third section 133 of the lid 130 folded against a bottom surface of the box 120. The lid 130 is further configured to have a closed position, as shown in FIG. 2A-B, with the first section 131 and the second section 132 of the lid 130 positioned over the top of the box 120, and the third section 133 of the lid 130 folded against a front wall of the box 120 and held in place by a magnetic attraction between magnetic material in the third section 133 of the lid 130 and magnetic material in the front wall of the box 120. At least one of the magnetic material in the lid 130 and the magnetic material in the box 120 is a magnet, such as a permanent magnet, but the other magnetic material may or may not be a magnet and may simply be a magnetic material such as steel.

Figure 3:
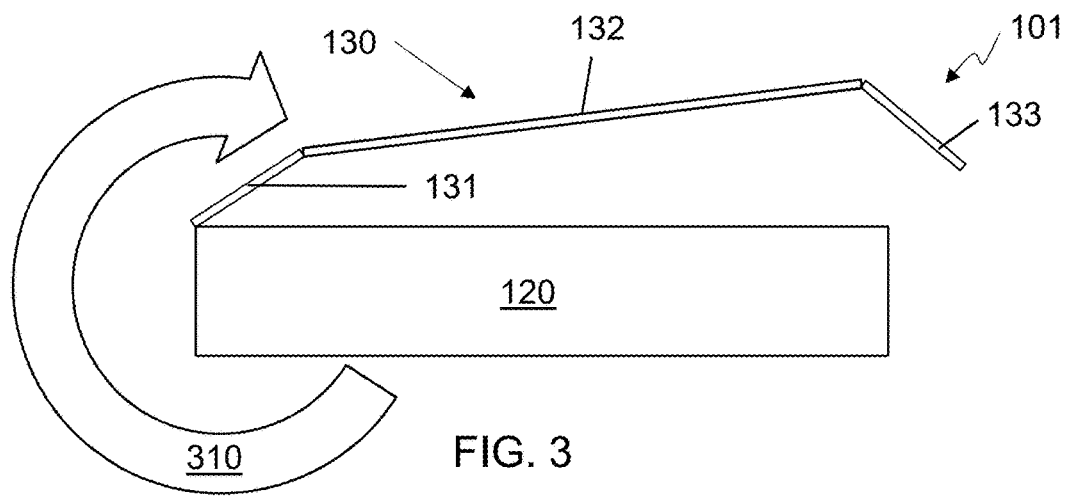
FIG. 3 shows the closing of the cover of the embodiment of the tool case.

FIG. 3 shows the closing of a cover 130 of the embodiment of the tool case 101. In closing the lid 130, the lid 130 starts in the open position. In the open position as shown in FIG. 1D, the first section 131 of the lid 130 is folded against a back wall of the box 120, and the second section 132 and the third section 133 of the lid 130 are folded against a bottom surface of the box 120. To close the box, the lid 130 is rotated 310 around the back of box 120 to position the lid 130 into a closed position as shown in FIG. 2B. In the closed position, the lid 130 has the first section 131 and the second section 132 of the lid 130 positioned over the top of the box 130, and the third section 133 of the lid 130 folded against a front wall of the box 120 and held in place by a magnetic attraction between magnetic material in the third section 133 of the lid 130 and magnetic material in the front wall of the box 120.

Figure 4:
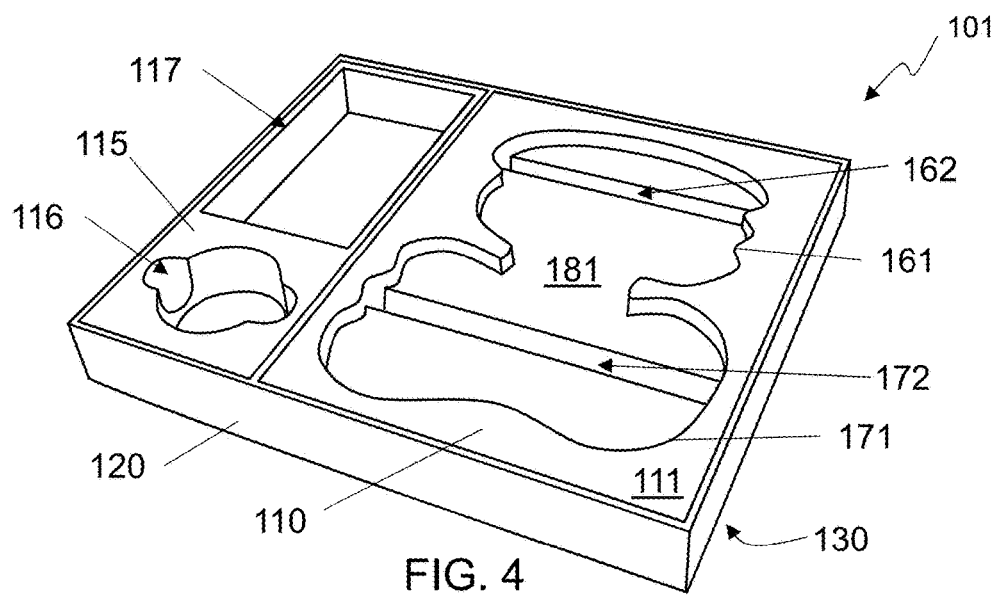
FIG. 4 shows a perspective view of the embodiment of the tool case without massage tools.

FIG. 4 shows a perspective view of the embodiment of the tool case 101 without massage tools 600, 700. The tool case 101 includes a structure 110 with a top surface 111. The top surface 111 has a recess 181 shaped to receive and situate at least one substantially flat tool in a horizontal position. In this embodiment, the recess 181 has a first portion 161 shaped to receive and situate a first substantially flat tool and a second portion 171 shaped to receive and situate a second substantially flat tool. In some embodiments, the top surface 111 also includes a second recess shaped to receive and situate the second substantially flat tool in a horizontal position instead of shaping the recess 181 to hold two tools. The structure includes a slot 162 shaped to receive and situate the substantially flat tool in an angled position extending away from the top surface 111, and the embodiment shown includes a second slot 172 shaped to receive and situate the second substantially flat tool in a second angled position extending away from the top surface 111. The structure 110 of the embodiment consists of a first injection-molded plastic part.

The embodiment of the tool case 101 also includes a box 120 that includes a cavity configured to accept the structure 110, and the structure 110 may be inserted into the cavity. The tool case 101 also includes an accessory-holding structure 115 configured to fit in the second cavity. The accessory-holding structure 115 is inserted into the second cavity. The accessory-holding structure 115 has a top surface with a third recess 116 shaped to receive and situate a first accessory and a fourth recess 117 shaped to receive and situate a second accessory. The accessory-holding structure 115 of the embodiment consists of a second injection-molded plastic part.

Figure 5A:
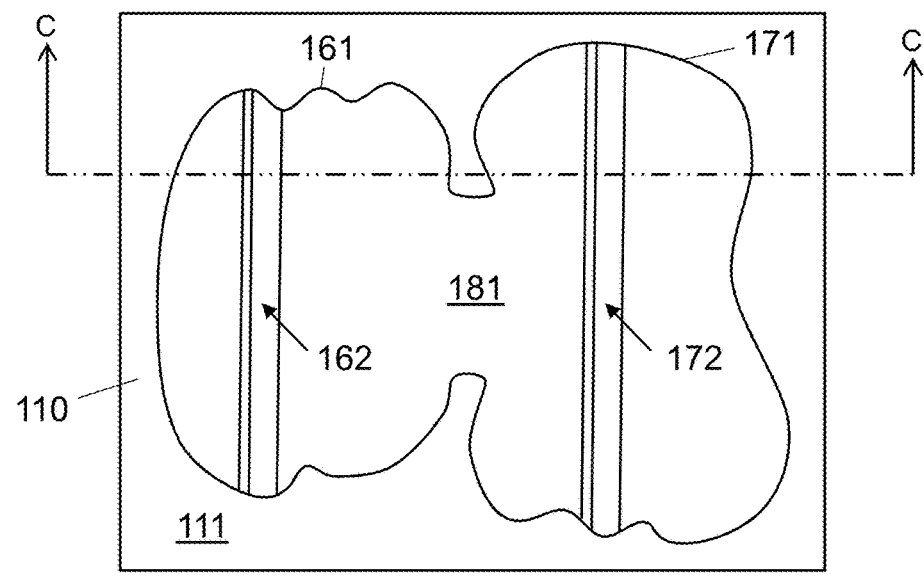
FIGS. 5A and 5B show top and cross-sectional views, respectively, of an embodiment of a structure to hold massage tools in either a storage or display position.
Figure 5B:
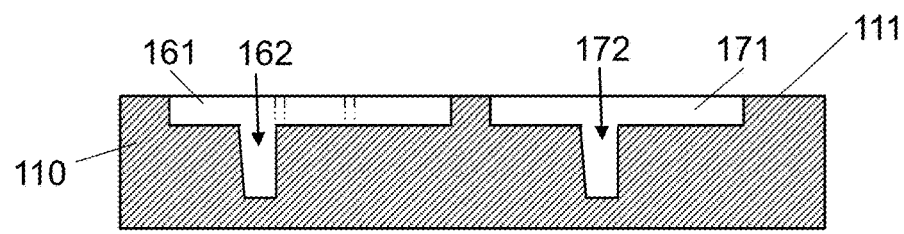

FIG. 5A shows a top view of an embodiment of a structure 110 to hold massage tools in either a storage or display position. FIG. 5B shows a cross-sectional view of the structure 110 at position C:C shown in FIG. 5A. The structure 110 includes a top surface 111 that has a recess 181 shaped to receive and situate a first substantially flat tool in a horizontal position relative to the top surface 111 in a first portion 161 of the recess 181 and receive and situate a second substantially flat tool in a horizontal position relative to the top surface 111 in a second portion 171 of the recess 181. The recess 181 can have a single common depth or can have different depths for the first portion 161 and the second portion 171. The recess 181 can have any depth, depending on the embodiment, but in some embodiments, the recess 181 has a depth between 50% and 150% of a thickness of one of the substantially flat tools.

The structure 110 also includes a slot 162 shaped to receive and situate the first substantially flat tool in a first angled position extending away from the top surface 111 and an additional slot 172 shaped to receive and situate the second substantially flat tool in a second angled position extending away from the top surface 111. In the embodiment of the structure 110, both the slot 162 and the additional slot 172 are disposed completely within the recess 181. The two slots 162, 172 can each have any depth depending on the embodiment, and may or may not have the same depth. In some embodiments, the slot 162 can have a slot depth of between 5% and 50% of a height of the substantially flat tool, and a slot width of at least 90% of a thickness of the substantially flat tool with the width not exceeding a sum of the slot depth and the thickness of the substantially flat tool. If the slot width is less than 100% of the thickness of the tool, the structure 110 is made of a flexible material, such as a foam material, to allow the slot 162 to expand as the tool is inserted into the slot 162.

In at least one embodiment, the recess 181 has a depth of between 120% and 95% of a thickness of the substantially flat tool, with the slot having a slot depth of between 15% and 35% of a height the substantially flat tool with a width that does not exceed 200% of the thickness of the substantially flat tool. In some embodiments, the recess 181 and the slots 162, 172 both taper away from the top surface 111 of the structure 110 so that the bottom of the recess 181 is somewhat smaller than the top of the recess 181 and the bottoms of the slots 162, 172 are smaller than the respective tops of the slots 162, 172.

The structure 110 can be made from any type of suitable material and formed using any process suitable for the materials used. A single type of material or multiple types of material may be used to form the structure 110. While FIG. 5B shows a solid material for the structure 110, in some embodiments the structure 110 may be a sheet of material formed into the appropriate shape, or the structure 110 may have hollow portions. The structure 110 may or may not have all four sides and may or may not have a flat bottom surface as shown in FIG. 5B. In some embodiments, the structure 110 includes a molded plastic part, such as, but not limited to, an injection molded part or a vacuformed plastic sheet. In other embodiments, the structure 110 may be formed from one or more layers of a polymer foam material, each layer cut to an appropriate shape and bonded together to form the structure. In other embodiments, the structure 110 may be carved from wood for decorative purposes. In yet another embodiment, the structure 110 may be formed from metal, such as a cast part, a machined part, or a stamped part.

Figure 6A:
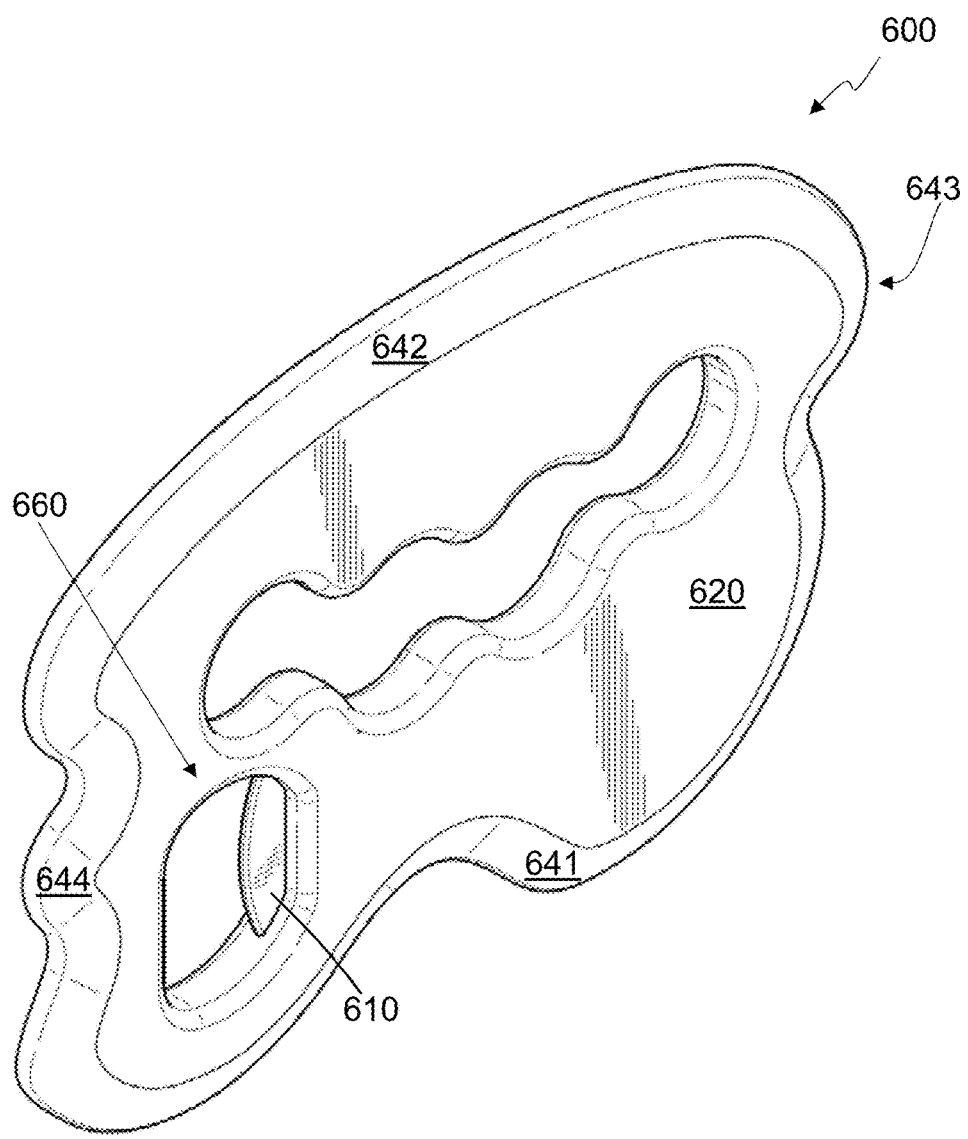
Figure 6B:
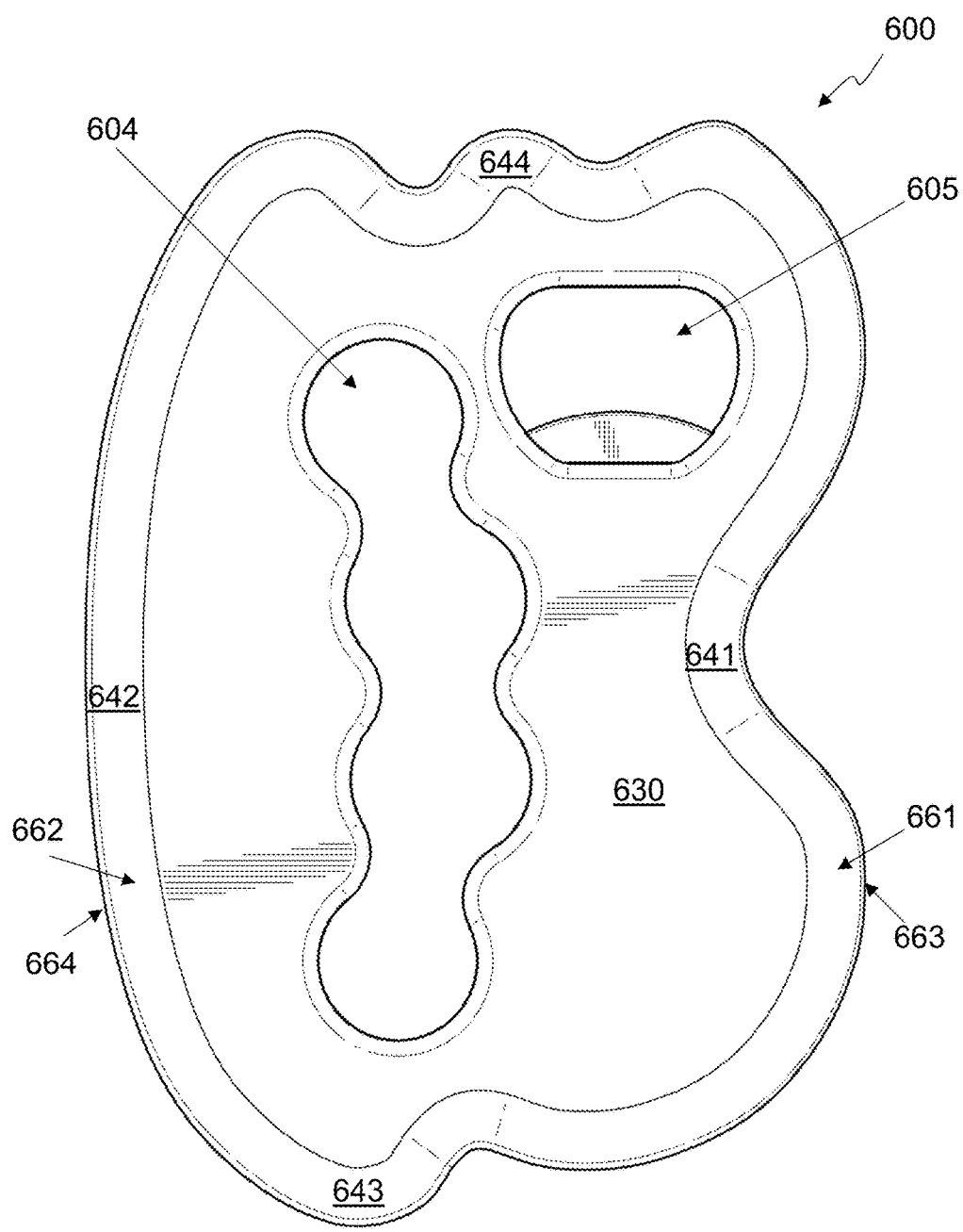

FIG. 6A-F show different views of a first embodiment of a massage tool 600 with an integrated bottle opener 660. The massage tool 600 can be considered an IASTM tool. FIG. 6A is a front, right, and top perspective view of a first embodiment of a massage tool 600 and FIG. 6B shows a left side elevation view of the first embodiment of a massage tool. FIGS. 6C, 6D, 6E, and 6F show a rear elevation view, a front elevation view, a top plan view, and a bottom plan view of the first embodiment of a massage tool, respectively. The following discussion applies equally to FIG. 6A-F, with various parts of the massage tool 600 shown more clearly in some views than in other views. While common reference numbers are used for these drawings, not every feature is labeled with the reference number in every drawing in which it is visible to help enhance the clarity of the drawings.

The massage tool 600 has a first side 630 and a second side 620 of the massage tool 600, and one or more massage surfaces 641-644 coupling the first side 630 of the massage tool 600 to the second side 620 of the massage tool 600. Any type, or types, of material can be used for the massage tool 600, including, but not limited to any type of plastic, various alloys of steel, other metals or alloys of metals, wood, ceramic materials, and composite materials. The first embodiment of the massage tool 600 includes one or more plastic parts that may be fabricated from an alloy blend of polybutylene terephthalate and polycarbonate (PBT+PC) plastic to provide good chemical resistance and excellent impact resistance and a weight plate 610 fabricated from stainless steel about 1.5 mm thick with a mass of between 45 grams (g) and 60 g, to provide a total mass of between 180 g and 195 g for the massage tool 600.

In the first embodiment, the first side 630 and the second side 620 of the massage tool 600 are planar and parallel, although other embodiments may have sides that are convex, concave, or have a more complex shape. The first embodiment of the massage tool 600 has a thickness of about 9 mm, a length of about 150 mm, and a height of about 106 mm, making the massage tool substantially flat. The first embodiment of the massage tool 600 includes a finger hole 604 through the first side 630, the weight plate 610, and the second side 620. The finger hole 604 is sized to allow one or more fingers to extend through the massage tool 600 and can be considered a gripping structure of the massage tool 600. The first embodiment of the massage tool 600 also includes a bottle opener 660 that includes an opening 605 through the first side 630 and the second side 620, and a portion of the weight plate 610 protruding into the opening 604 and adapted to catch an edge of a bottle cap.

In the first embodiment of the massage tool 600, the massage surface 641-644 extends around the massage tool 600. In embodiments, the massage surface may be divided into any number of sections that may be continuous or have discontinuities between sections. The massage surface 641-644 of the massage tool 600 has a bottom massage surface 641 with a concave contour and a top massage surface 642 with a convex contour, where the contour is the curve created by a silhouette of that portion of the massage surface as viewed from the side. The massage tool 600 also has a rear massage surface and a front massage surface 644 with complex contours having subsections with concave contours and subsections convex contours.

Figure 7A:
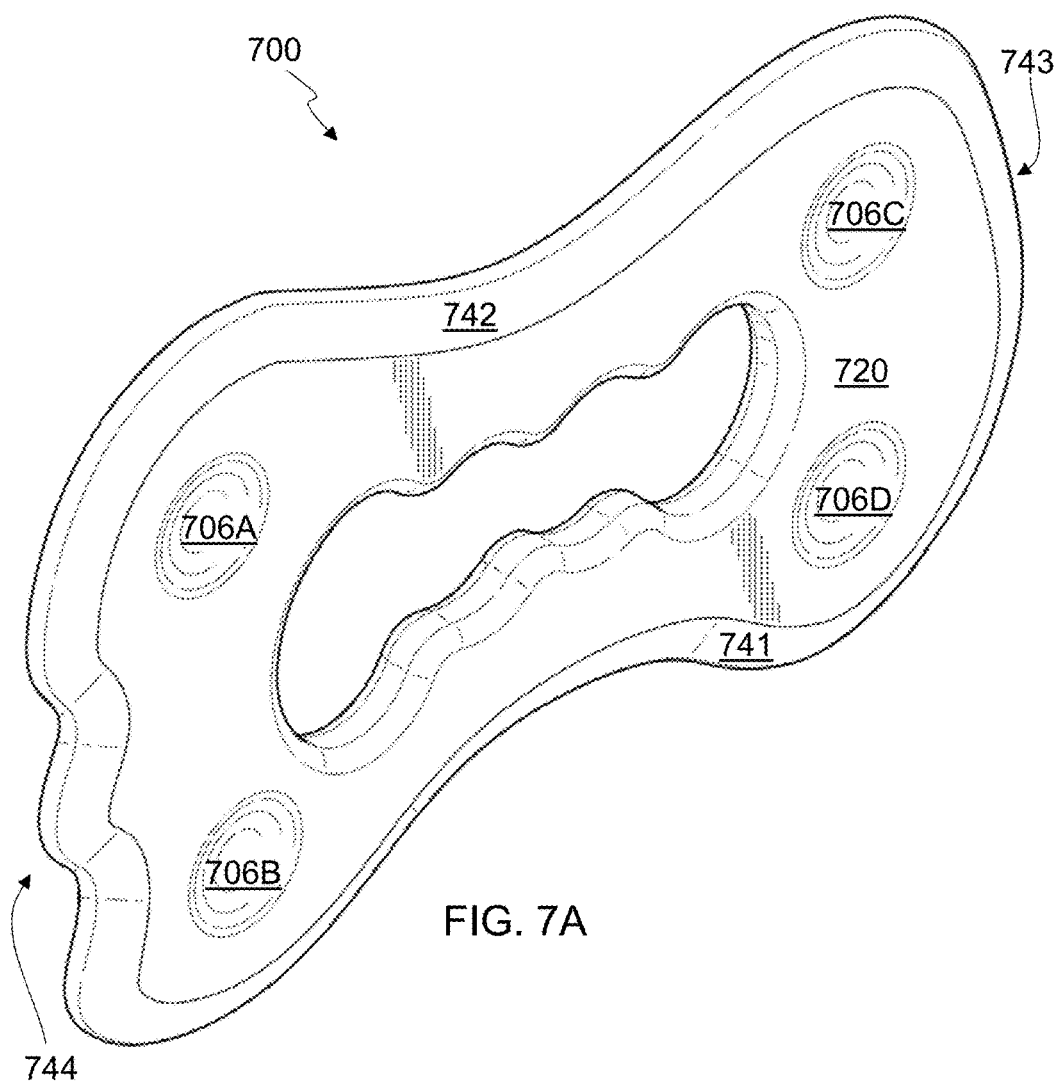
Figure 7B:
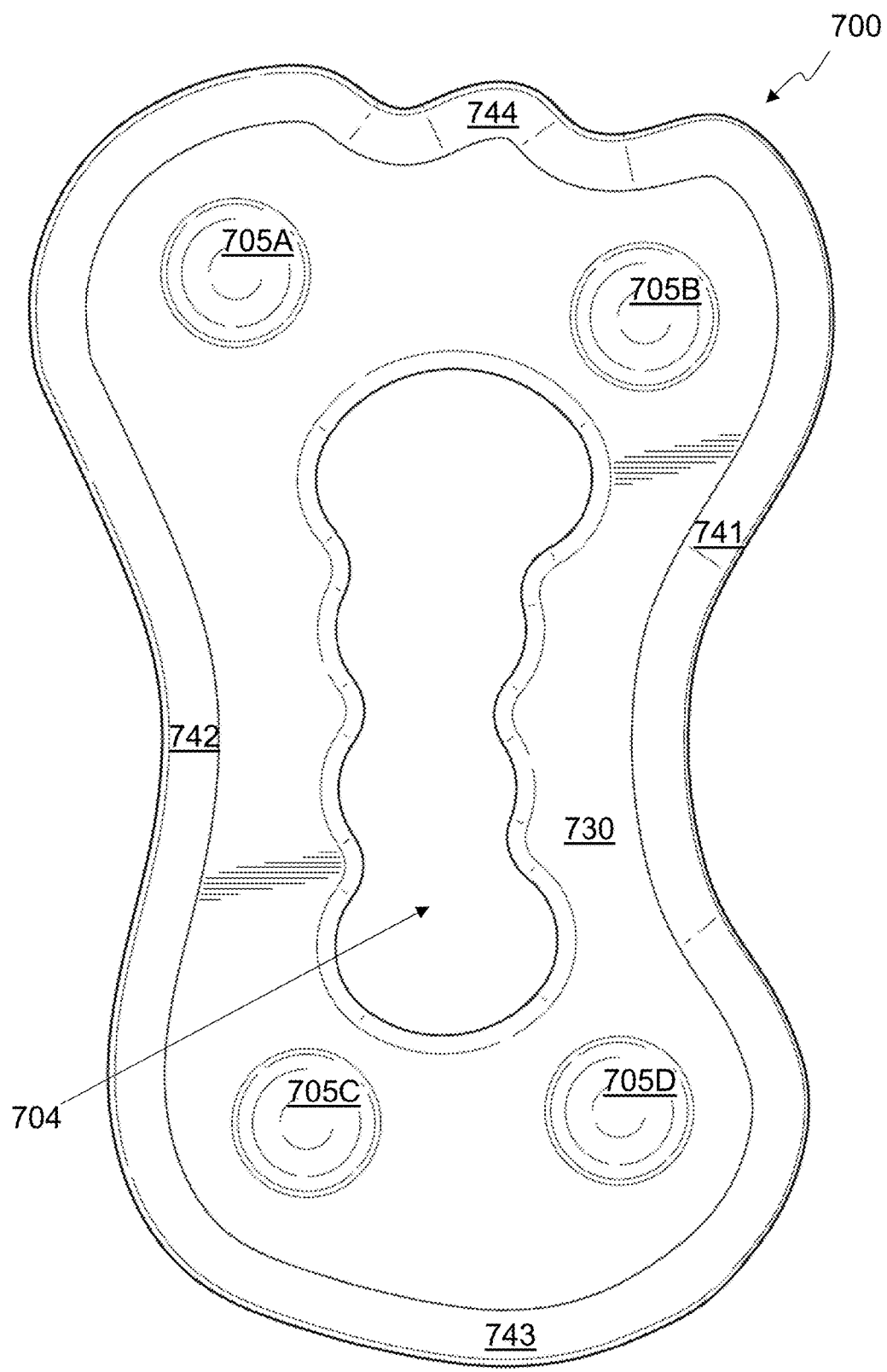

FIG. 7A-F show different views of a second embodiment of a massage tool 700. FIG. 7A is a front, right and top perspective view of a second embodiment of a massage tool 700 and FIG. 7B shows a left side elevation view of the second embodiment of a massage tool. FIGS. 7C, 7D, 7E, and 7F show a rear elevation view, a front elevation view, a top plan view, and a bottom plan view of the second embodiment of a massage tool 700, respectively. The following discussion applies equally to FIG. 7A-F, with various parts of the massage tool 700 shown more clearly in some views than in other views. While common reference numbers are used for these drawings, not every feature is labeled with the reference number in every drawing in which it is visible to help enhance the clarity of the drawings.

The massage tool 700 has a first side 730, a second side 720, and one or more massage surfaces 741-744 coupling the first side 730 of the massage tool 700 to the second side 720 of the massage tool 700. Any type of material in any combination can be used for the massage tool 700, including, but not limited to any type of plastic, various alloys of steel, other metals or alloys of metals, wood, ceramic materials, and composite materials. In the second embodiment of the massage tool 700, the first side 730 is made from a first stainless steel part, the second side 720 is made from a second stainless steel part, and the massage surfaces 741-744 include portions of both the first stainless steel part and the second stainless steel part.

In the second embodiment of the massage tool 700, the first side 730 and the second side 720 are planar and parallel to each other. The second embodiment of the massage tool 700 has a thickness of about 9 mm, a length of about 184 mm, and a height of about 114 mm. The second embodiment of the massage tool 700 includes a finger hole 704 through the first side 730 and the second side 720. The finger hole 704 is sized to allow one or more fingers to extend through the massage tool 700 and can be considered a gripping structure of the massage tool 700. The massage tool 700 also includes gripping dimples 705A-D on the first side 730 and gripping dimples 706A-D on the second side 720 that can also be considered gripping structures of the massage tool 700.

In the second embodiment of the massage tool 700, the massage surfaces 741-744 extend around the massage tool 700. The massage surfaces 741-744 of the massage tool 700 include a bottom massage surface 741 with a concave contour and a top massage surface 742 with a concave contour, where the contour is the curve created by a silhouette of that portion of the massage surface as viewed from the side. The massage tool 700 also includes a rear massage surface 743 with a convex contour and a front massage surface 744 with a complex contour having subsections with concave contours and subsections with convex contours.

FIG. 8A shows a top view of a second embodiment of a structure 810 to hold tools in either a storage or a display position. FIG. 8B shows a cross-sectional view of the structure 810 at the position B:B shown in FIG. 8A. The structure 810 has a top surface 811 with a recess 820 shaped to receive and situate a substantially flat tool, in this embodiment the triangle tool 890 shown in FIG. 8C-D, in a horizontal position relative to the top surface. The structure 810 also includes a slot 830 shaped to receive and situate the substantially flat tool 890 in an angled position extending away from the top surface 811. In this embodiment, the slot 830 does not intersect with the recess 820. While the cross-sectional view of FIG. 8B shows the structure 810 to be solid, in other embodiments the structure 810 may be hollow or include hollow areas and may include any combination of the four sides and the bottom surfaces. The structure may be formed from any type of material, including, but not limited to metal, wood, hard plastics, soft plastics, or flexible polymer foam materials.

FIG. 8C shows a perspective view of the second embodiment of a tool case 800 with a tool 890 in a storage position, and FIG. 8D shows a perspective view of the second embodiment of the tool case 800 with the tool 890 in a display position. In the storage position, the tool 890 is horizontally situated in the recess 820, while in the display position the tool 890 is vertically situated in the slot 830. The tool case 800 includes the structure 810 and a cover 840. In some embodiments, the tool case 800 may also include a box to hold the structure 810, but in other embodiments, no box is included. The cover 840 is configured to alternately mate with the structure 810 in a closed position that covers the recess 820 and the slot 830, and an open position to expose the slot 830. The second embodiment of the cover 840 is a box-shaped lid with a top and four sides that is configured to slide over the top of the structure 810 for a closed position, or to slide over the bottom of the structure 810 for an open position.

Figures 9A, 9B:
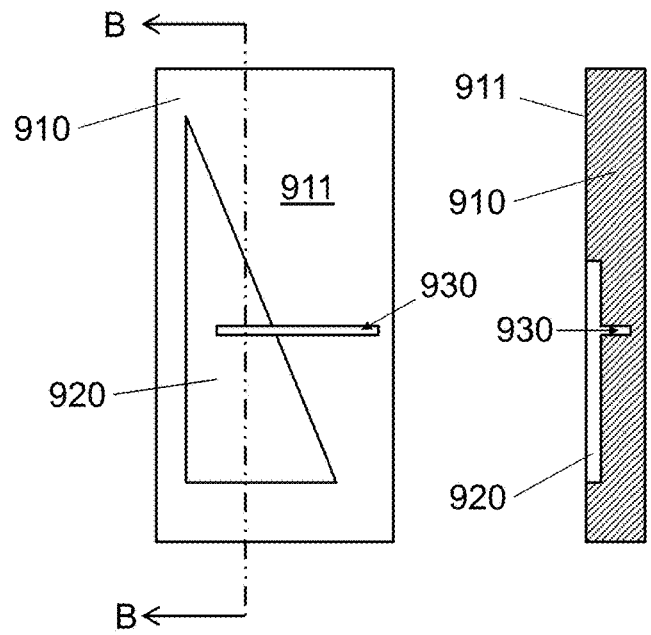
FIGS. 9A and 9B show top and cross-sectional views, respectively, of a third embodiment of a structure to hold tools in either a storage or display position.

FIG. 9A shows a top view of a third embodiment of a structure 910 to hold tools in either a storage or a display position. FIG. 9B shows a cross-sectional view of the structure 910 at the position B:B shown in FIG. 9A. The structure 910 has a top surface 911 with a recess 920 shaped to receive and situate a substantially flat tool, in this case the triangle tool 990 shown in FIG. 9C-D, in a horizontal position relative to the top surface. The structure 910 also includes a slot 930 shaped to receive and situate the substantially flat tool 990 in an angled position extending away from the top surface 911. In this embodiment, the slot 930 intersects with the recess 920. Thus, the slot 930 is disposed, at least in part, within the recess 920 in the top surface 911. While the cross-sectional view of FIG. 9B shows the structure 910 to be solid, in other embodiments, the structure 910 may be hollow or include hollow areas and may include any combination of the four sides and the bottom surfaces. The structure may be formed from any type of material including, but not limited to metal, wood, hard plastics, soft plastics, or flexible polymer foam materials.

Figures 9C, 9D:
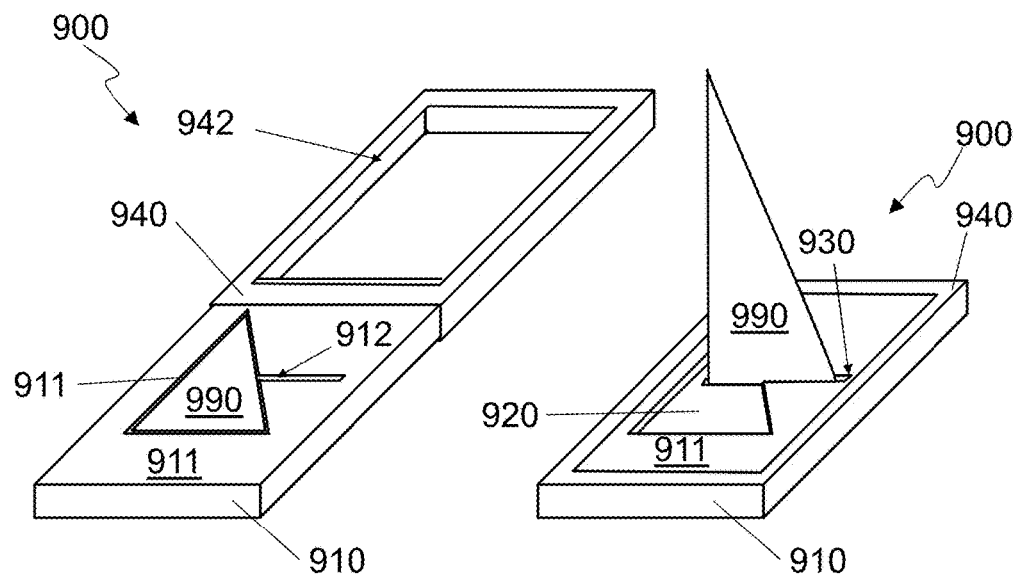
FIG. 9C shows a perspective view of a third embodiment of a tool case with a tool in a storage position.
FIG. 9D shows a perspective view of the third embodiment of the tool case with the tool in a display position.

FIG. 9C shows a perspective view of the third embodiment of a tool case 900 with a tool 990 in a storage position and FIG. 9D shows a perspective view of the third embodiment of the tool case 900 with the tool 990 in a display position. In the storage position, the tool 990 is horizontally situated in the recess 920, while in the display position the tool 990 is vertically situated in the slot 930. The tool case 900 includes the structure 910 and a cover 940. In some embodiments, the tool case 900 may also include a box to hold the structure 910, but in other embodiments, no box is included. The cover 940 is configured to alternately mate with the structure 910 in a closed position that covers the recess 920 and the slot 930, and an open position to expose the slot 930. The second embodiment of the cover 940 is a tube-shaped sleeve with a top, bottom, and two sides that is configured to slide over one end of the structure 910. The cover 940 has a hole 942 in the top that is large enough to expose the slot 930 if the cover 940 is slipped over the structure 910 with the hole 942 on the same side as the top surface 911, which constitutes an open position. If the cover 940 is slipped over the structure 910 with the hole 942 on the opposite side of the top surface 911, that is a closed position.

Figure 10:
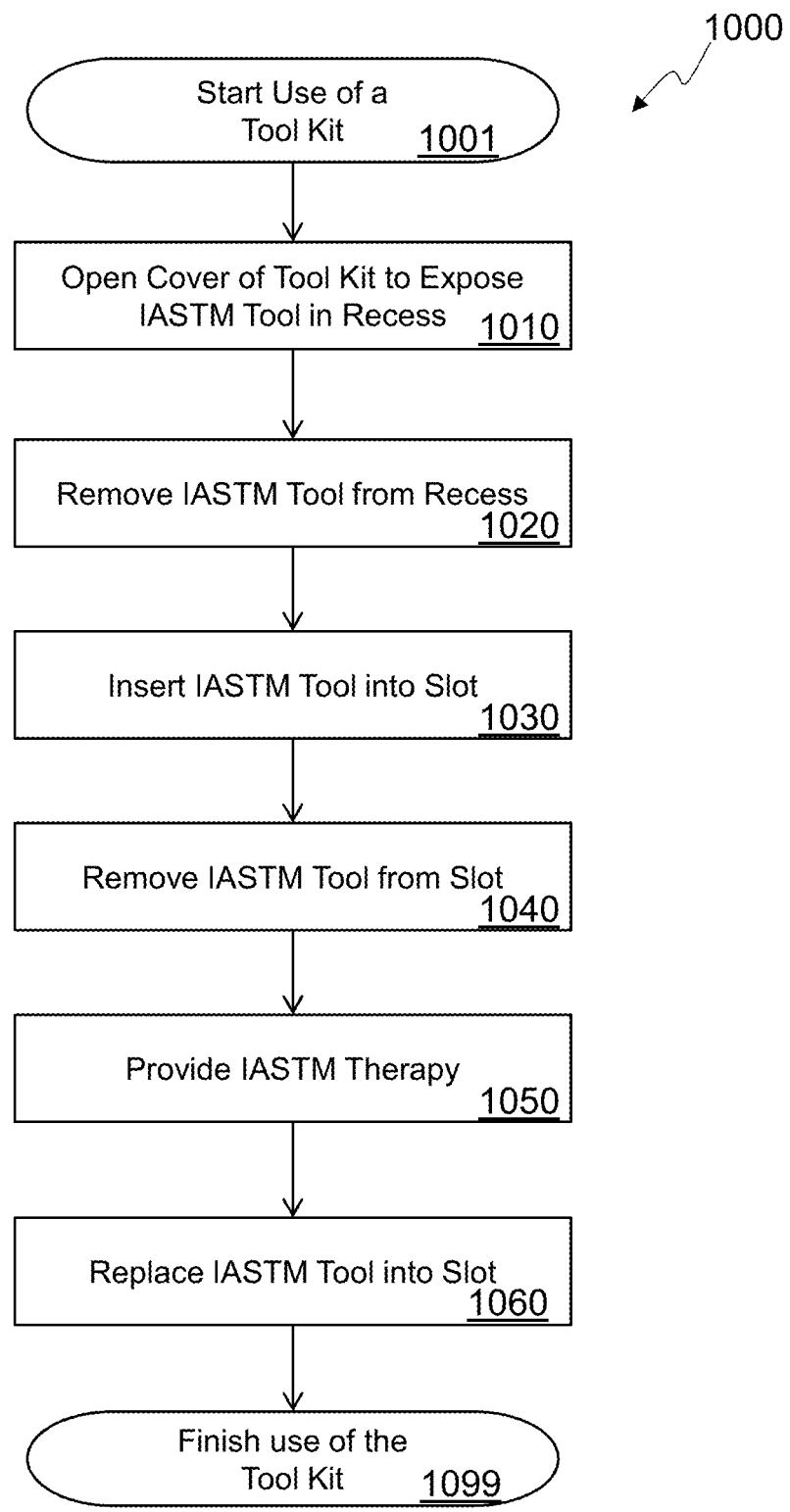
FIG. 10 shows a flowchart of an embodiment of a method of using a tool case for massage tools.

FIG. 10 shows a flowchart 1000 of an embodiment of a method of using a tool case for massage tools. The method starts with use of the tool kit at block 1001 and continues with opening a cover of the tool kit to reveal a substantially flat tool, such as an IASTM tool, horizontally situated in a recess in a top surface of a structure of the tool kit at block 1010. At block 1020 the substantially flat tool is removed from the recess and at block 1030, the substantially flat tool is inserted into a slot of the structure in an angled relationship to the top surface of the structure.

The substantially flat tool may be a massage tool, such as an instrument-assisted soft tissue manipulation (IASTM) tool, in some embodiments. In such embodiments, the method may optionally also include removing the IASTM tool from the slot at block 1040 and using the IASTM tool to provide IASTM therapy to a living mammal at block 1050. In some embodiments, the living mammal is a horse or a human. The IASTM tool is optionally replaced into the slot at block 1060 before the use of the tool kit is finished at block 1099.

In some embodiments, the opening of the cover of the tool kit at block 1010 also reveals a lubricant situated in an additional recess. In such embodiments, the method may also optionally include removing the lubricant from the additional recess and using the lubricant in conjunction with the IASTM therapy. In some embodiments, the opening of the cover of the tool kit at block 1010 also reveals an accessory situated in an additional recess. In such embodiments, the method may also optionally include removing the accessory from the additional recess and using the accessory in conjunction with providing a therapy to a living mammal.

Unless otherwise indicated, all numbers expressing quantities of elements, optical characteristic properties, and so forth used in the specification and claims are to be understood as being modified in all instances by the term "about." Accordingly, unless indicated to the contrary, the numerical parameters set forth in the preceding specification and attached claims are approximations that can vary depending upon the desired properties sought to be obtained by those skilled in the art utilizing various principles of the present disclosure. Recitation of numerical ranges by endpoints includes all numbers subsumed within that range (e.g. 1 to 5 includes 1, 2.78, π, and 5). As used in this specification and the appended claims, the singular forms "a", "an", and "the" include plural referents unless the content clearly dictates otherwise. Thus, for example, reference to an element described as "an opening" may refer to a single opening, two opening, or any other number of openings. As used in this specification and the appended claims, the term "or" is generally employed in its "and/or" inclusive sense, which includes the case where all the elements are included, unless the content clearly dictates otherwise. As used herein, the term "coupled" includes direct and indirect connections. Moreover, where first and second devices are coupled, intervening elements including active elements may be located there between. Any element in a claim that does not explicitly state "means for" performing a specified function, or "step for" performing a specified function, is not to be interpreted as a "means" or "step" clause as specified in 35 U.S.C. § 112(f).

The description of the various embodiments provided above is illustrative in nature and is not intended to limit the claims, their application, or their uses. Thus, different variations beyond those described herein are intended to be within the scope of the embodiments of the claims. Such variations are not to be regarded as a departure from the intended scope of the present disclosure. As such, the breadth and scope of the present invention should not be limited by the above-described exemplary embodiments, but should be defined only in accordance with the following claims and equivalents thereof.

What is claimed is:

1. A tool case comprising a structure with a top surface,
    the top surface having a recess shaped to receive and situate a substantially flat tool in a horizontal position relative to the top surface,
    the structure including a slot shaped to receive and situate the substantially flat tool in an angled position extending away from the top surface, the slot having a top opening width that is larger than a bottom width of the slot;
    a box-shaped element comprising the structure; and
    a lid divided into a first section, a second section, and a third section,
    a rear top edge of the element hingedly attached to an inner edge of the first section of the lid, an outer edge of the first section of the lid hingedly attached to an inner edge of the second section of the lid, and an outer edge of the second section of the lid hingedly attached to an inner edge of the third section of the lid,
    the first section of the lid and the third section of the lid each having a length about equal to a height of the element, and the second section of the lid having a length about equal to a difference between the length of the element and the height of the element, the lid configured to have an open position with the first section of the lid folded against a back wall of the element, and the second section of the lid and the third section of the lid folded against a bottom surface of the element, and the lid further configured to have a closed position with the first section of the lid and the second section of the lid laying over a top of the element, and the third section of the lid folded against a front wall of the element and held in place by a magnetic attraction between magnetic material in the third section of the lid and magnetic material in the front wall of the element.

2. The tool case of claim 1, the recess having a depth between 50% and 150% of a thickness of the substantially flat tool.

3. The tool case of claim 1, the slot configured to hold the substantially flat tool at an angle from the top surface of between 45 and 135 degrees.

4. The tool case of claim 1, the slot having a slot depth of between 5% and 50% of a height the substantially flat tool and a slot width of at least 90% of a thickness of the substantially flat tool and does not exceed a sum of the slot depth and the thickness of the substantially flat tool.

5. The tool case of claim 1, the slot disposed, at least in part, within the recess in the top surface.

6. The tool case of claim 1, the structure comprising a molded plastic part.

7. The tool case of claim 1, the top surface further having a second recess shaped to receive and situate a second substantially flat tool in a horizontal position relative to the top surface, and the structure further including a second slot shaped to receive and situate the second substantially flat tool in a second angled position extending away from the top surface.

8. The tool case of claim 1, further comprising a third recess configured to receive and situate an accessory.

9. The tool case of claim 1, further comprising a box comprising a cavity configured to accept the structure, the structure inserted therein.

10. The tool case of claim 1, further comprising a cover, the cover configured to alternately mate with the structure in a first position that covers the recess and the slot, and a second position to expose the slot.

11. An instrument assisted soft tissue mobilization (IASTM) system comprising:
    a first substantially flat massage tool; and
    a case comprising a structure with a top surface, the top surface having a first recess shaped to receive and situate the first substantially flat tool in a horizontal position relative to the top surface, and the structure including a first slot having a top opening width that is larger than a bottom width of the first slot to receive and situate the substantially flat tool in an angled position extending away from the top surface;
    the first recess shaped to also receive and situate a second substantially flat tool in a horizontal position relative to the top surface, and the structure further including a second slot shaped to receive and situate the second substantially flat tool in a second angled position extending away from the top surface;
    wherein both the first slot and the second slot are disposed completely within the first recess.

12. The IASTM system of claim 11, the first recess having a depth between 120% and 95% of a thickness of the substantially flat tool and the first slot having a slot depth of between 15% and 35% of a height the substantially flat tool and a slot width that does not exceed 200% of the thickness of the substantially flat tool.

13. The IASTM system of claim 11, the first substantially flat massage tool comprising a gripping structure, and the first slot having a slot depth configured to expose the gripping structure of the substantially flat massage tool when the substantially flat massage tool is inserted into the slot.

14. The IASTM system of claim 11, further comprising:
    a box separated into a first cavity and a second cavity, the first cavity configured to accept the structure, the structure inserted therein;
    a lid divided into a first section, a second section, and a third section,
    a rear top edge of the box hingedly attached to an inner edge of the first section of the lid, an outer edge of the first section of the lid hingedly attached to an inner edge of the second section of the lid, and an outer edge of the second section of the lid hingedly attached to an inner edge of the third section of the lid,
    the first section of the lid and the third section of the lid each having a length about equal to a height of the box, and the second section of the lid having a length about equal to a difference between the length of the box and the height of the box,
    the lid configured to have an open position with the first section of the lid folded against a back wall of the box, and the second section of the lid and the third section of the lid folded against a bottom surface of the box, and
    the lid further configured to have a closed position with the first section of the lid and the second section of the lid laying over a top of the box, and the third section of the lid folded against a front wall of the box and held in place by a magnetic attraction between magnetic material in the third section of the lid and magnetic material in the front wall of the box.

15. An instrument assisted soft tissue mobilization (IASTM) system comprising:
    a first substantially flat massage tool;
    a case comprising a structure with a top surface, the top surface having a first recess shaped to receive and situate the first substantially flat tool in a horizontal position relative to the top surface, and the structure including a first slot having a top opening width that is larger than a bottom width of the first slot to receive and situate the substantially flat tool in an angled position extending away from the top surface;
    a box separated into a first cavity and a second cavity, the first cavity configured to accept the structure, the structure inserted therein;
    an accessory;
    an additional structure configured to fit in the second cavity and inserted therein, the additional structure having a top surface with a third recess shaped to receive and situate the accessory, the accessory inserted into the third recess;
    a lid divided into a first section, a second section, and a third section,
    a rear top edge of the box hingedly attached to an inner edge of the first section of the lid, an outer edge of the first section of the lid hingedly attached to an inner edge of the second section of the lid, and an outer edge of the second section of the lid hingedly attached to an inner edge of the third section of the lid,
    the first section of the lid and the third section of the lid each having a length about equal to a height of the box, and the second section of the lid having a length about equal to a difference between the length of the box and the height of the box, the lid configured to have an open position with the first section of the lid folded against a back wall of the box, and the second section of the lid and the third section of the lid folded against a bottom surface of the box, and the lid further configured to have a closed position with the first section of the lid and the second section of the lid laying over a top of the box, and the third section of the lid folded against a front wall of the box and held in place by a magnetic attraction between magnetic material in the third section of the lid and magnetic material in the front wall of the box.

16. The IASTM system of claim 15, wherein the accessory is selected from a group consisting of wipes, tissues, massage oil, lotion, skin moisturizer, hand sanitizer, kinesiology tape, bandages, and antibiotic cream.

17. The IASTM system of claim 15, the first recess having a depth between 120% and 95% of a thickness of the substantially flat tool and the first slot having a slot depth of between 15% and 35% of a height the substantially flat tool and a slot width that does not exceed 200% of the thickness of the substantially flat tool.

18. The IASTM system of claim 15, the first substantially flat massage tool comprising a gripping structure, and the first slot having a slot depth configured to expose the gripping structure of the substantially flat massage tool when the substantially flat massage tool is inserted into the slot.

19. The IASTM system of claim 15, the first slot disposed completely within the first recess in the top surface.

20. The IASTM system of claim 15, the top surface further having a second recess shaped to receive and situate a second substantially flat tool in a horizontal position relative to the top surface, and the structure further including a second slot shaped to receive and situate the second substantially flat tool in a second angled position extending away from the top surface.

* * * * *